(12) United States Patent
Hoop et al.

(10) Patent No.: US 7,413,730 B2
(45) Date of Patent: Aug. 19, 2008

(54) COSMETIC AND DERMATOLOGICAL LIGHT PROTECTION FORMULATIONS

(75) Inventors: Kerstin Hoop, Pinneberg (DE); Heike Lerg, Hamburg (DE); Anja Sabine Mueller, Rümpel (DE); Bente Nissen, Hamburg (DE); Melanie Steinforth, Hamburg (DE); Martin Sugár, Hamburg (DE)

(73) Assignee: Beiersdorf AG, Hamburg (DE)

( * ) Notice: Subject to any disclaimer, the term of this patent is extended or adjusted under 35 U.S.C. 154(b) by 502 days.

(21) Appl. No.: 11/039,376

(22) Filed: Jan. 19, 2005

(65) Prior Publication Data
US 2006/0034785 A1 Feb. 16, 2006

(30) Foreign Application Priority Data
Jan. 19, 2004 (DE) ................ 10 2004 003 001

(51) Int. Cl.
*A61Q 17/04* (2006.01)
*A61Q 17/00* (2006.01)
*A61Q 19/04* (2006.01)
*A61Q 19/00* (2006.01)
*A61K 8/02* (2006.01)

(52) U.S. Cl. .................. 424/59; 424/60; 424/400; 424/401

(58) Field of Classification Search ............. 424/59, 424/60, 400, 401
See application file for complete search history.

(56) References Cited

U.S. PATENT DOCUMENTS

| 5,989,528 | A | 11/1999 | Tanner et al. |
| 5,989,529 | A | 11/1999 | Kaplan |
| 6,821,934 | B1 | 11/2004 | Bleckmann et al. |
| 2002/0146438 | A1 | 10/2002 | Bleckmann et al. |

FOREIGN PATENT DOCUMENTS

| DE | 198 54 497 A1 | 12/1999 |
| DE | 198 41 797 A1 | 3/2000 |
| DE | 198 41 798 A1 | 3/2000 |
| DE | 198 55 153 A1 | 5/2000 |
| DE | 101 55 865 A1 | 5/2003 |
| WO | 00/06110 | 2/2000 |

OTHER PUBLICATIONS

Brochure "1999 . . . L'année de l'éclipse solaire", Mar. 1999.
Letter from DIPTA to Mme Guyollot dated Jun. 30, 1999.
Printout webpage http:/www.gndp.com regarding "Capital Soleil Mexoryl XL Sun Block", Date Published: Jul. 17, 2003.
Printout webpage http:/www.gndp.com regarding "Color Control Milk", Date Published: May 15, 2002.
Printout webpage http:/www.gndp.com regarding "Color Control Children's Sun Cream", Date Published: Apr. 26, 2002.
Brochure "Arlacel P 135, polymeric emulsifier ICI Surfactants" (42-8E/3966.2$^{nd}$ Ed.S.DH/Apr. 1997, pp. 1-3 and 8-15.
Cosmetic & Toiletries, Mar. 1987, pp. 23-35.
Richlinie 93/35/EWG des Rates vom 14. Juni 1993 (Directive 93/35/EWG of the Council of the European Community dated Jun. 14, 1993 regarding cosmetic agents).
Printout webpage http:/www.gndp.com/Sinatra/gndp/search_results dated Jun. 8, 2007.
Printout webpage http:/www.gndp.com/Sinatra/gndp/search_results/&item_id=375501 dated Jun. 8, 2007.
Letter from MINTEL to Merck KgaA dated Oct. 16, 2007 regarding GNDP Record ID 216817.
Letter from MINTEL to Merck KgaA dated Oct. 16, 2007 regarding Mintel Products Database.
Printout "Ciba® Sunscreen Simulator" dated Sep. 18, 2007.
Merck presentation "Wasserfestigkeits-Test" (Water Resistance Test), Oct. 16, 2007.
DIN 67502, Feb. 2005.
Merck UV-Spectrum "5 mg PEG+Dipolyhydroxystearate in 100 ml 2-Propanol", undated.
Parfumerie und Kosemetik, vol. 80, No. 3/99 pp. 17, 18, 22, 23.
Product brochure BASF Uvinul® grades, Aug. 1995.
Printout webpage http:/www.gndp.com/Sinatra/gndp/search_results/&item_id=86632?single regarding " Face Care Day Cream", Date Published: Feb. 2001.
Licht und Haut: Braunung, Lichtschutz, Pflege 4$^{th}$ ed. Govi-Verlag 1988, pp. 204-206 (relating to water resistance).

*Primary Examiner*—Shelley A. Dodson
(74) *Attorney, Agent, or Firm*—Greenblum & Bernstein, P.L.C.

(57) ABSTRACT

The invention is a light protective cosmetic or dermatological preparation, comprising
(a) PEG-30 dipolyhydroxystearate,
(b) 2-ethylhexyl 2-cyano-3,3-diphenylacrylate,
(c) at least one dibenzoylmethane derivative and
(d) at least 2% by weight of titanium dioxide particles, based on the total weight of the preparation,
and is free from water-soluble UV-A filter substances.

20 Claims, No Drawings

COSMETIC AND DERMATOLOGICAL LIGHT PROTECTION FORMULATIONS

CROSS-REFERENCE TO RELATED APPLICATIONS

This application claims the benefit of German Patent Application Serial No DE 10 2004 003 001.4, filed Jan. 19, 2004, the contents of which are hereby incorporated by reference.

FIELD OF THE INVENTION

The present invention relates to cosmetic and dermatological light protection preparations, in particular it relates to cosmetic and dermatological formulations with increased UV-A protection performance.

BACKGROUND OF THE INVENTION

The harmful effect of the ultraviolet part of solar radiation on the skin is generally known. Depending on their particular wavelength, the rays have different effects on the skin as an organ:

The so-called UV-C radiation with a wavelength between 100 and 280 nm is absorbed by the ozone layer in the Earth's atmosphere and accordingly is not found in the solar spectrum. It is therefore of no physiological importance during sunbathing.

The so-called UV-B region is between 290 nm and 320 nm. UV-B rays are essentially responsible for the long-lasting tanning of the skin, but can at the same time cause an erythema, simple sunburn or even burns of greater or lesser severity. Chronic photodamage, photodermatoses and Herpes solaris can also be caused by UV-B radiation.

It has for a long time been incorrectly assumed that long-wave UV-A radiation with a wavelength between 320 nm and 400 nm only has a negligible biological effect and that, correspondingly, the UV-B rays are responsible for most photodamage to the human skin. However, in the meantime, numerous studies have demonstrated that UV-A radiation is much more hazardous than UV-B radiation with regard to the triggering of photodynamic, specifically phototoxic reactions and chronic changes in the skin. The harmful influence of UV-B radiation can also be further intensified by UV-A radiation.

Thus, it has, inter alia, been found that even UV-A radiation suffices under very normal everyday conditions to harm, within a short time, the collagen and elastin fibers which are of essential importance for the structure and strength of the skin. The consequences are chronic photo-induced changes in the skin—the skin "ages" prematurely. The clinical appearance of skin aged by light includes, for example, wrinkles and lines, and also an irregular, furrowed relief. In addition, the areas affected by photo-induced skin ageing can have irregular pigmentation. The formation of brown spots, keratoses and even carcinomas or malignant melanomas is also possible. Skin aged prematurely by everyday UV exposure is, moreover, characterized by lower activity of the Langerhans cells and slight, chronic inflammation.

Approximately 90% of the ultraviolet radiation which reaches the Earth consists of UV-A rays. While UV-B radiation varies widely depending on numerous factors (e.g. time of year and time of day or degree of latitude), UV-A radiation remains relatively constant day to day irrespective of the time of year and time of day or geographical factors. At the same time, the majority of UV-A radiation penetrates into the living epidermis, while approximately 70% of UV-B rays are retained by the horny layer.

The relatively recent findings concerning the effect of UV-A rays on the skin have led to increased attention now being devoted to protective measures for this ray range. In practice, no sunscreen product is complete any more without an effective UV-A filter effect, and pure UV-B filter preparations are rare.

When applying a sunscreen to the skin, the ultraviolet rays can be weakened through two effects: firstly, by reflection and scattering of the rays at the surface of pulverulent solids (physical light protection) and, secondly, by absorption on chemical substances (chemical light protection). Depending on which wavelength region is absorbed, a distinction is made between UV-B filters (absorption range 280 to 320 nm), UV-A filters (absorption range 320 to 400 nm) and broadband filters (absorption range 290 to about 380 nm).

To protect against UV-B radiation, numerous compounds are known, the absorption maximum of which should be around 308 nm as far as possible since this is the highest erythema effectiveness of solar radiation. Typical UV-B filters are, for example, derivatives of 3-benzylidenecamphor, of 4-aminobenzoic acid, of cinnamic acid, of salicylic acid, of benzophenone, and also of 2-phenylbenzimidazole.

Some compounds are also known for protecting against UV-A radiation, such as, in particular, dibenzoylmethane derivatives. However, dibenzoylmethane derivatives are generally not photostable, as a result of which cosmetic or dermatological preparations with a content of this substance should also comprise certain UV stabilizers.

Besides the pure UV-A or UV-B filters, there are substances which cover both regions. This group of broadband filters includes, for example, asymmetrically substituted s-triazine compounds, such as, for example, 2,4-bis{[4-(2-ethylhexyloxy)-2-hydroxyl]phenyl}-6-(4-methoxyphenyl)-1,3,5-triazine (INCI: BisEthylhexyloxyphenol Methoxyphenyl Triazine), certain benzophenones, such as, for example, 2-hydroxy-4-methoxybenzophenone (INCI: Benzophenone 3) or 2,2'-methylenebis(6-(2H-benzotriazole-2-yl)-4-(1,1,3,3-tetramethylbutyl)phenol) (INCI: Methylene Bis-Benzotriazolyl Tetramethylenebutylphenol).

In general, the light absorption behavior of light protection filter substances is very well known and documented, especially as there are positive lists for the use of such substances in most industrialized countries, which impose very strict standards on the documentation. Since, in order to characterize a filter substance, not only is the position of the absorption maximum important, but primarily the absorption range, absorption spectra are recorded for each substance. However, the absorbance values can at best be a guide for the concentration of the substances in the finished formulations since interactions with ingredients of the skin or of the surface of the skin itself may give rise to imponderables. In addition, it is usually difficult to estimate beforehand how uniformly and thickly the filter substance is distributed in and on the horny layer of the skin.

To test the UV-A protection performance, use is usually made of the IPD method (IPD=immediate pigment darkening). Similarly to the determination of the sun protection factor, this method gives a value which indicates how much longer the skin protected with the light protection composition can be irradiated with UV-A radiation until the pigmentation which occurs is the same as for the unprotected skin.

The use concentration of known light protection filter substances which exhibit a high filter effect particularly also in the UV-A region is, however, often limited—especially in combination with other substances to be dissolved. In order, for example, to be able to use large amounts of oil-soluble UV filter substances, a very large oil phase (>about 35% by weight) would be required. However, the hydrophobic phase of an emulsion—for example of a W/O emulsion—could not be chosen to be arbitrarily large since the size of the phases also decisively influences the stability of an emulsion. If a large oil phase (of more than about 35% by weight) is desired, according to the prior art, stabilizers such as waxes or further emulsifiers have to be used in order to obtain an emulsion with a long-term stability of several years. However, a disadvantage of this procedure is that the emulsions become relatively solid as a result and can no longer be distributed as well—particularly on hairy skin.

A further method known according to the prior art for preparing light protection preparations with very high light protection factors (LPF greater than 25) consists in combining UV filter substances such that the entire amount of UV filter is not in the oil phase of the emulsion, which is of course only possible if water-soluble UV filter substances are also used. A disadvantage of such emulsions which comprise water-soluble UV filter substances is that these are usually only water-resistant to a limited extent.

The water resistance of light protection formulations is, however, attributed particular importance since most sunscreen compositions are applied in the vicinity of water or during sporting activity (sweating). A water-resistant sunscreen composition protects the user not only after bathing, but also protects him against sunburn during bathing. It is a widespread misconception that water offers good or even adequate protection against ultraviolet radiation. Rather, investigations have shown that even 1 m below the surface of the water, the transmittance for UV-B rays is about 50%. It is therefore advisable for those who participate in water sports, who, for example, swim, surf or snorkel, and in particular children, who often play for hours at or in the water, to also protect the skin against overly intense and excessive solar irradiation with a sun product which adheres well and can only be rinsed off with difficulty by (salt) water and perspiration.

For the purposes of optimum water resistance, the omission of water-soluble UV filters would therefore be desirable.

SUMMARY OF THE INVENTION

It was therefore an object of the present invention to arrive, in a simple and cost-effective manner, at preparations which achieve high UV-A protection performance and at the same time are characterized by good water resistance and good distributability.

It was surprising and unforeseeable by the person skilled in the art that a light protective cosmetic or dermatological preparation, characterized in that it comprises
(a) PEG-30 dipolyhydroxystearate,
(b) 2-ethylhexyl 2-cyano-3,3-diphenylacrylate,
(c) at least one dibenzoylmethane derivative and
(d) at least 2% by weight of titanium dioxide particles (based on the total weight of the preparation), the preparation being free from water-soluble UV-A filter substances, would overcome the disadvantages of the prior art.

The preparations according to the invention are entirely satisfactory preparations in every respect which exhibit very good sensory and cosmetic properties, such as, for example, distributability on the skin or the ability to absorb into the skin. They are further characterized by very good light protection effectiveness, an exceptionally high UV-A protection performance and by excellent skin compatibility coupled with excellent skin care data.

It is particularly surprising and one of the particular advantages of the present invention that the use of water-soluble UV-A filters can be totally dispensed with. Further advantages of the present invention are that, despite a high oil phase fraction of more than 35% by weight (based on the total weight of the preparation), no further emulsifier or coemulsifier is necessary and that in addition the fraction of further stabilizers, such as waxes, can be chosen to be very low (less than 1.5% by weight, ideally less than 1% by weight). In this way, despite a high oil phase, a flowable formulation (with a viscosity of <10 000 mPa·s—determinable using a Haake viscotester VT-02 at 25° C.) is obtained and thus good distributability and optimum light protection are ensured.

The particularly high UV-A protection is achieved through the special combination of UV-A filters of a filter liquid at room temperature (25° C.) (2-ethylhexyl 2-cyano-3,3-diphenylacrylate), a solid lipophilic filter (dibenzoylmethane derivative) and a pigmentary filter ($TiO_2$).

DETAILED DESCRIPTION OF THE INVENTION

Particularly advantageous preparations for the purposes of the present invention comprise more than 3% by weight, in particular more than 10% by weight—in each case based on the total weight of the preparation—of UV-A filter substances according to the invention. It is also advantageous according to the invention if titanium dioxide has the highest (weight) fraction in the UV-A filter combination according to the invention.

The substance combinations according to the invention have a surprising synergistic effect, i.e. have a superadditive effect relative to the individual components. They are photostable without further additives and exhibit a surprisingly high protection performance in the UV-A region.

PEG-30 dipolyhydroxystearate is sold by Uniquema under the trade name ARLACEL® P135.

2-Ethylhexyl 2-cyano-3,3-diphenylacrylate (INCI: Octocrylene) is available from BASF under the name Uvinul®N 539 T.

An advantageous dibenzoylmethane derivative for the purposes of the present invention is in particular 4-(tert-butyl)-4'-methoxydibenzoylmethane (CAS No. 70356-09-1), which is sold by Givaudan under the trade name Parsol® 1789 and by Merck under the trade name Eusolex® 9020. Also advantageous is 2,2'-methylenebis(6-(2H-benzotriazol-2-yl)-4-(1,1,3,3-tetramethylbutyl)phenol). The dibenzoylmethane derivative or derivatives can be used advantageously in each case individually or in any combinations with one another.

According to the invention, the titanium dioxide particles may advantageously be surface-treated ("coated"), the intention being to form or retain, for example, a hydrophilic, amphiphilic or hydrophobic character. This surface treatment can consist in providing the pigments with a thin hydrophilic and/or hydrophobic inorganic and/or organic coating by methods known per se. For the purposes of the present invention, the various surface coatings may also comprise water.

For the purposes of the present invention, the titanium dioxide particles may also advantageously be used in the form of commercially obtainable oily or aqueous predispersions. Dispersion auxiliaries and/or solubility promoters may advantageously be added to these predispersions.

Titanium dioxide particles and predispersions of titanium dioxide particles which are advantageous according to the invention are obtainable under the following trade names from the companies listed:

| Trade name | Coating | Manufacturer |
|---|---|---|
| MT-100TV | Aluminium hydroxide/stearic acid | Tayca Corporation |
| MT-100Z | Aluminium hydroxide/stearic acid | Tayca Corporation |
| Eusolex T-2000 | Alumina/simethicone | Merck KGaA |

-continued

| Trade name | Coating | Manufacturer |
| --- | --- | --- |
| Titanium dioxide T805 (Uvinul TiO$_2$) | Octyltrimethylsilane | Degussa |
| Tioveil AQ 10PG | Alumina/silica | Solaveil/Uniquema |

For the purposes of the present invention, the preparations are preferably in the form of water-in-oil ("W/O") emulsions.

The cosmetic or dermatological light protection formulations according to the invention can have the customary composition and be used for cosmetic or dermatological light protection, and also for the treatment, care and cleansing of the skin and/or of the hair and as a make-up product in decorative cosmetics.

Depending on their formulation, cosmetic or topical dermatological compositions for the purposes of the present invention can, for example, be used as skin protection cream, cleansing milk, day or night cream etc. It is optionally possible and advantageous to use the compositions according to the invention as a base for pharmaceutical formulations.

For use, the cosmetic and dermatological preparations are applied to the skin and/or the hair in an adequate amount in the manner customary for cosmetics.

The cosmetic and dermatological preparations according to the invention can comprise cosmetic auxiliaries as are customarily used in such preparations, e.g. preservatives, preservative aids, complexing agents, bactericides, perfumes, substances for preventing or increasing foaming, dyes, pigments which have a coloring action, thickeners, moisturizing and/or humectant substances, fillers which improve the feel on the skin, fats, oils, waxes or other customary constituents of a cosmetic or dermatological formulation, such as alcohols, polyols, polymers, foam stabilizers, electrolytes, organic solvents or silicone derivatives.

Advantageous preservatives for the purposes of the present invention are, for example, formaldehyde donors (such as, for example, DMDM hydantoin, which is available, for example, under the trade name Glydant™ from Lonza), iodopropyl butylcarbamates (e.g. those available under the trade names Glycacil-L, Glycacil-S from Lonza, and/or Dekaben LMB from Jan Dekker), parabens (i.e. alkyl p-hydroxybenzoates, such as methyl-, ethyl-, propyl- and/or butylparaben), phenoxyethanol, ethanol, benzoic acid and the like. In addition, the preservative system according to the invention also usually advantageously comprises preservative aids, such as, for example, octoxyglycerol, glycine soya etc.

Advantageous complexing agents for the purposes of the present invention are, for example, EDTA, [S,S]-ethylenediamine disuccinate (EDDS), which is available, for example, under the trade name Octaquest from Octel, pentasodium ethylenediamine tetramethylenephosphonate, which is available, for example, under the trade name Dequest 2046 from Monsanto and/or iminodisuccinic acid, which is available, inter alia, from Bayer AG under the trade names Iminodisuccinate VP OC 370 (about 30% strength solution) and Baypure CX 100 solid.

Particularly advantageous preparations are also obtained when antioxidants are used as additives or active ingredients. According to the invention, the preparations advantageously comprise one or more antioxidants. Favorable, but nevertheless optional, antioxidants which may be used are all antioxidants customary or suitable for cosmetic and/or dermatological applications. For the purposes of the present invention, water-soluble antioxidants may be used particularly advantageously, such as, for example, vitamins, e.g. ascorbic acid and derivatives thereof.

Preferred antioxidants are also vitamin E and derivatives thereof, and vitamin A and derivatives thereof. The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant or the antioxidants, it is advantageous to choose their respective concentrations from the range from 0.001 to 10% by weight, based on the total weight of the formulation. If vitamin A or vitamin A derivatives, or carotenes or derivatives thereof are the antioxidant or the antioxidants, it is advantageous to choose their respective concentrations from the range from 0.001 to 10% by weight, based on the total weight of the formulation.

It is particularly advantageous when the cosmetic preparations according to the present invention comprise cosmetic or dermatological active ingredients, preferred active ingredients being antioxidants which can protect the skin against oxidative stress.

Further advantageous active ingredients for the purposes of the present invention are natural active ingredients and/or derivatives thereof, such as, for example, α-lipoic acid, phytoene, D-biotin, coenzyme Q10, α-glucosylrutin, carnitine, carnosine, natural and/or synthetic isoflavonoids, creatine, taurine and/or β-alanine, and 8-hexadecene-1,16-dicarboxylic acid (dioic acid, CAS number 20701-68-2; provisional INCI name Octadecenedioic acid).

Formulations according to the invention which comprise, for example, known antiwrinkle active ingredients, such as flavone glycosides (in particular α-glycosylrutin), coenzyme Q10, vitamin E and/or derivatives and the like are particularly advantageously suitable for the prophylaxis and treatment of cosmetic or dermatological changes in the skin, as arise, for example, during the skin ageing (such as, for example, dryness, roughness and formation of dryness wrinkles, itching, reduced refatting (e.g. after washing), visible vascular dilations (telangiectases, cuperosis), flaccidity and formation of wrinkles and lines, local hyperpigmentation, hypopigmentation and incorrect pigmentation (e.g. age spots), increased susceptibility to mechanical stress (e.g. cracking) and the like). In addition, they are advantageously suitable to counter the appearance of dry or rough skin.

The water phase of the preparations according to the invention can advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, butylene glycol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, and in particular one or more thickeners, which may advantageously be chosen from the group consisting of silicon dioxide, aluminium silicates or polysaccharides or derivatives thereof, e.g. hyaluronic acid, xanthan gum, hydroxypropylmethylcellulose, particularly advantageously from the group of polyacrylates, preferably a polyacrylate from the group of so-called Carbopols [from Goodrich], for example Carbopol grades 980, 981, 1382, 2984, 5984, ETD 2020, ETD 2050, Ultrez 10, in each case individually or in combination.

In addition, the preparations according to the invention can advantageously also comprise self-tanning substances, such as, for example, dihydroxyacetone and/or melanin derivatives in concentrations of from 1% by weight to 8% by weight, based on the total weight of the preparation.

In addition, the preparations according to the invention can advantageously also comprise repellents for protection against flies, ticks and spiders and the like. For example, N,N-diethyl-3-methylbenzamide (trade name: Meta-delphene, "DEET"), dimethyl phthalate (trade name: Palatinol M, DMP) and in particular ethyl 3-(N-n-butyl-N-acetylamino)propionate (available under the trade name Insekt Repellent® 3535 from Merck) are advantageous. The repellents can either be used individually or in combination.

Moisturizers is the term used to refer to substances or mixtures of substances which impart to cosmetic or dermatological preparations the property, following application or distribution on the surface of the skin, of reducing moisture release by the horny layer (also called trans-epidermal water loss (TEWL)) and/or of positively influencing hydration of the horny layer.

Advantageous moisturizers for the purposes of the present invention are, for example, glycerol, lactic acid and/or lactates, in particular sodium lactate, butylene glycol, propylene glycol, biosaccharide gum-1, glycine soya, ethylhexyloxyglycerol, pyrrolidone carboxylic acid and urea. In addition, it is particularly advantageous to use polymeric moisturizers from the group of water-soluble and/or water-swellable and/or water-gelable polysaccharides. Hyaluronic acid, chitosan and/or a fucose-rich polysaccharide, which is filed in the Chemical Abstracts under the registry number 178463-23-5 and which is available, for example, under the name Fucogel® 1000 by SOLABIA S.A., for example, are particularly advantageous. Moisturizers can advantageously also be used as anti-wrinkle active ingredients for the prophylaxis and treatment of cosmetic or dermatological changes in the skin, as arise, for example, during skin ageing.

The cosmetic or dermatological preparations according to the invention can also advantageously, but not necessarily, comprise fillers, which, for example, further improve the sensory and cosmetic properties of the formulations and, for example, bring about or enhance a velvety or silky feel on the skin. Advantageous fillers for the purposes of the present invention are starch and starch derivatives (such as, for example, tapioca starch, distarch phosphate, aluminium or sodium starch octenylsuccinate and the like), pigments which have neither a primarily UV filter effect nor a coloring effect (such as, for example, boron nitride etc.) and/or Aerosils® (CAS No. 7631-86-9).

The oil phase of the formulations according to the invention is advantageously chosen from the group of polar oils, for example from the group of lecithins and of fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, cocoglyceride, olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil and the like.

Also advantageous according to the invention are, for example, natural waxes of animal and vegetable origin, such as, for example, beeswax and other insect waxes, and berry wax, sheabutter and/or lanolin (woolwax). It is also advantageous to choose wax components from the group of glycerides, in particular from the group of triglycerides. For the purposes of the present invention, $C_{18-36}$ triglyceride, which is available under the trade name Syncrowax HGLC from Croda GmbH, is particularly advantageous.

Further advantageous polar oil components for the purposes of the present invention may also be chosen from the group of esters of saturated and/or unsaturated, branched and/or unbranched alkanecarboxylic acids of chain length from 3 to 30 carbon atoms and saturated and/or unsaturated, branched and/or unbranched alcohols of chain length from 3 to 30 carbon atoms, and from the group of esters of aromatic carboxylic acids and saturated and/or unsaturated, branched and/or unbranched alcohols of chain length from 3 to 30 carbon atoms. Such ester oils can then advantageously be chosen from the group consisting of octyl palmitate, octyl cocoate, octyl isostearate, octyldodecyl myristate, octyidodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can advantageously be chosen from the group of dialkyl ethers and dialkyl carbonates, advantageous examples being dicaprylyl ether (Cetiol OE) and/or dicaprylyl carbonate, for example that available under the trade name Cetiol CC from Cognis.

It is also preferred to choose the oil component or oil components from the group consisting of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythritol hexacaprylate/hexacaprate, propylene glycol monoisostearate, tricaprylin, dimethyl isosorbide. It is particularly advantageous if the oil phase of the formulations according to the invention has a content of $C_{12-15}$-alkyl benzoate or consists entirely of this.

Advantageous oil components are also, for example, butyloctyl salicylate (for example that available under the trade name Hallbrite BHB from CP Hall), hexadecyl benzoate and butyloctyl benzoate and mixtures thereof (Hallstar AB) and/or diethylhexyl naphthalate (Hallbrite TQ or Corapan TQ from H&R).

Any mixtures of such oil and wax components can also be used advantageously for the purposes of the present invention.

In addition, the oil phase can likewise advantageously also comprise nonpolar oils, for example those which are chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils, or consist entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a chain-like and/or reticular manner and the remaining valencies of the silicon are saturated by hydrocarbon radicals (in most cases methyl groups, more rarely ethyl, propyl, phenyl groups, etc.). Systematically, the silicone oils are referred to as polyorganosiloxanes. The methyl-substituted polyorganosiloxanes, which represent the most important compounds of this group in terms of amount and are characterized by the following structural formula

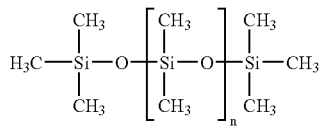

are also referred to as polydimethylsiloxane or Dimethicone (INCI). Dimethicones exist in various chain lengths and with various molecular weights.

Particularly advantageous polyorganosiloxanes for the purposes of the present invention are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopenta siloxane), which are also referred to as Cyclomethicone in accordance with INCI, amino-modified silicones (INCI: Amodimethicones) and silicone waxes, e.g. polysiloxane-polyalkylene copolymers (INCI: Stearyl Dimethicones and Cetyl Dimethicones) and dialkoxydimethylpolysiloxanes (Stearoxy Dimethicones and Behenoxy Stearyl Dimethicones), which are available as various Abil wax grades from Th. Goldschmidt. However, other silicone oils can also be used advantageously for the purposes of the present invention, for example cetyldimethicone, hexamethylcyclotrisiloxane, polydimethylsiloxane, poly(methylphenylsiloxane).

The preparations according to the invention can also advantageously comprise one or more substances from the following group of siloxane elastomers, for example in order to increase the water resistance and/or the light protection factor of the products:
(a) siloxane elastomers which contain the units $R_2SiO$ and $RSiO_{1.5}$ and/or $R_3SiO_{0.5}$ and/or $SiO_2$,
   where the individual radicals R, in each case independently of one another, are hydrogen, $C_{1-24}$-alkyl (such as, for example, methyl, ethyl, propyl) or aryl (such as, for example, phenyl or tolyl), alkenyl (such as, for example, vinyl), and the weight ratio of the units $R_2SiO$ to $RSiO_{1.5}$ is chosen from the range from 1:1 to 30:1;
(b) siloxane elastomers which are insoluble and swellable in silicone oil and which are obtainable by the addition reaction of an organopolysiloxane (1) which contains silicon-bonded hydrogen with an organopolysiloxane (2) which contains unsaturated aliphatic groups,
   where the quantitative amounts used are chosen such that the amount of hydrogen in the organopolysiloxane (1) or in the unsaturated aliphatic groups of the organopolysiloxane (2)
     is in the range from 1 to 20 mol % when the organopolysiloxane is noncyclic and
     is in the range from 1 to 50 mol % when the organopolysiloxane is cyclic.

For the purposes of the present invention, the siloxane elastomer or elastomers are advantageously present in the form of spherical powders or in the form of gels.

Siloxane elastomers present in the form of spherical powders which are advantageous according to the invention are those with the INCI name Dimethicone/Vinyl Dimethicone Crosspolymer, for example that available from DOW CORNING under the trade names DOW CORNING 9506 Powder.

It is particularly preferred when the siloxane elastomer is used in combination with oils from hydrocarbons of animal and/or vegetable origin, synthetic oils, synthetic esters, synthetic ethers or mixtures thereof.

It is very particularly preferred when the siloxane elastomer is used in combination with unbranched silicone oils which are liquid or pasty at room temperature or cyclic silicone oils or mixtures thereof. Organopolysiloxane elastomers with the INCI name Dimethicone/Polysilicone-11, very particularly the Gransil grades obtainable from Grant Industries Inc. GCM, GCM-5, DMG-6, CSE gel, PM-gel, LTX, ININ gel, AM-18 gel and/or DMCM-5 are particularly advantageous.

It is very extremely preferred when the siloxane elastomer is used in the form of a gel of siloxane elastomer and a lipid phase where the content of the siloxane elastomer in the gel is 1 to 80% by weight, preferably 0.1 to 60% by weight, in each case based on the total weight of the gel.

It is advantageous for the purposes of the present invention to choose the total amount of the siloxane elastomers (active content) from the range from 0.01 to 10% by weight, advantageously from 0.1 to 5% by weight, in each case based on the total weight of the formulation.

The cosmetic and dermatological preparations according to the invention can comprise dyes and/or color pigments, particularly when they are in the form of decorative cosmetics. The dyes and color pigments can be chosen from the corresponding positive list in the Cosmetics Directive or the EC list of cosmetic colorants. In most cases, they are identical to dyes approved for foods. Advantageous color pigments are, for example, titanium dioxide, mica, iron oxides (e.g. $Fe_2O_3$, $Fe_3O_4$, FeO(OH)) and/or tin oxide. Advantageous dyes are, for example, carmine, Prussian blue, chromium oxide green, ultramarine blue and/or manganese violet. It is particularly advantageous to choose the dyes and/or the color pigments from the *Rowe Colour Index, $3^{rd}$ Edition, Society of Dyers and Colourists*, Bradford, England, 1971.

If the formulations according to the invention are in the form of products which are used on the face, it is favorable to choose one or more substances from the following group as the dye: 2,4-dihydroxyazobenzene, 1-(2'-chloro-4'-nitro-1'-phenylazo)-2-hydroxynaphthalene, Ceres red, 2-(sulpho-1-naphthylazo)-1-naphthol-4-sulphonic acid, calcium salt of 2-hydroxy-1,2'-azonaphthalene-1'-sulphonic acid, calcium and barium salts of 1-(2-sulpho-4-methyl-1-phenylazo)-2-naphthylcarboxylic acid, calcium salt of 1-(2-sulpho-1-naphthylazo)-2-hydroxynaphthalene-3-carboxylic acid, aluminium salt of 1-(4-sulpho-1-phenylazo)-2-naphthol-6-sulphonic acid, aluminium salt of 1-(4-sulpho-1-naphthylazo)-2-naphthol-3,6-disulphonic acid, 1-(4-sulpho-1-naphthylazo)-2-naphthol-6,8-disulphonic acid, aluminium salt of 4-(4-sulpho-1-phenylazo)-1-(4-sulphophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalonedisulphonic acid, aluminium salt of indigodisulphonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochineal. Also advantageous for the purposes of the present invention are formulations with a content of pearlescent pigments. Preference is given in particular to the types of pearlescent pigments listed below:
1. Natural pearlescent pigments, such as, for example,
   "pearlessence" (guanine/hypoxanthin mixed crystals from fish scales) and
   "mother-of-pearl" (ground mussel shells)
2. Monocrystalline pearlescent pigments, such as, for example, bismuth oxychloride (BiOCl)

3. Layer-substrate pigments: e.g. mica/metal oxide

Bases for pearlescent pigments are, for example, pulverulent pigments or castor oil dispersions of bismuth oxychloride and/or titanium dioxide, and bismuth oxychloride and/or titanium dioxide on mica. The lustre pigment listed under CIN 77163, for example, is particularly advantageous.

Also advantageous are, for example, the following types of pearlescent pigments based on mica/metal oxide:

| Group | Coating/layer thickness | Colour |
|---|---|---|
| Silver-white pearlescent pigments | $TiO_2$: 40-60 nm | Silver |
| Interference pigments | $TiO_2$: 60-80 nm | Yellow |
| | $TiO_2$: 80-100 nm | Red |
| | $TiO_2$: 100-140 nm | Blue |
| | $TiO_2$: 120-160 nm | Green |
| Colour lustre pigments | $Fe_2O_3$ | Bronze |
| | $Fe_2O_3$ | Copper |
| | $Fe_2O_3$ | Red |
| | $Fe_2O_3$ | Red-violet |
| | $Fe_2O_3$ | Red-green |
| | $Fe_2O_3$ | Black |
| Combination pigments | $TiO_2/Fe_2O_3$ | Gold shades |
| | $TiO_2/Cr_2O_3$ | Green |
| | $TiO_2$/Prussian blue | Deep blue |
| | $TiO_2$/carmine | Red |

Particular preference is given, for example, to the pearlescent pigments obtainable from Merck under the trade names Timiron, Colourona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. $SiO_2$ particles coated with, for example, $TiO_2$ and $Fe_2O_3$ ("ronaspheres"), which are sold by Merck and are particularly suitable for the optical reduction of fine lines, are advantageous.

It can, moreover, be advantageous to dispense completely with a substrate such as mica. Particular preference is given to iron pearlescent pigments prepared without the use of mica. Such pigments are obtainable, for example, under the trade name Sicopearl Kupfer 1000 from BASF.

In addition, also particularly advantageous are effect pigments which are obtainable under the trade name Metasomes Standard/Glitter in various colors (yellow, red, green, blue) from Flora Tech. The glitter particles are present here in mixtures with various auxiliaries and dyes (such as, for example, the dyes with the Color Index (CI) numbers 19140, 77007, 77289, 77491).

The dyes and pigments may be present either individually or in a mixture, and can be mutually coated with one another, different coating thicknesses generally giving rise to different color effects. The total amount of dyes and color-imparting pigments is advantageously chosen from the range from, for example, 0.1% by weight to 30% by weight, preferably from 0.5 to 15% by weight, in particular from 1.0 to 10% by weight, in each case based on the total weight of the preparations.

For the purposes of the present invention, it is also advantageous to provide cosmetic and dermatological preparations whose main purpose is not protection against sunlight, but which nevertheless have a content of further UV protection substances. Thus, for example, UV-A and/or UV-B filter substances are usually incorporated into daycreams or make-up products. UV protection substances, like antioxidants and, if desired, preservatives, also constitute effective protection of the preparations themselves against spoilage. Also favorable are cosmetic and dermatological preparations in the form of a sunscreen.

Accordingly, for the purposes of the present invention, the preparations can preferably comprise further UV-A, UV-B and/or broadband filter substances. The formulations can, but do not necessarily, optionally comprise one or more organic and/or inorganic pigments as UV filter substances, which may be present in the water phase and/or the oil phase.

In addition, the preparations according to the invention can also advantageously be in the form of so-called oil-free cosmetic or dermatological emulsions, which comprise a water phase and at least one UV filter substance which is liquid at room temperature as a further phase.

For the purposes of the present invention, particularly advantageous UV filter substances which are liquid at room temperature are homomethyl salicylate (INCI: Homosalate), 2-ethylhexyl 2-hydroxybenzoate (2-ethylhexyl salicylate, octyl salicylate, INCI: Salicylate) Octyl and esters of cinnamic acid, preferably 2-ethylhexyl 4-methoxycinnamate (INCI: Octyl Methoxycinnamate) and isopentyl 4-methoxycinnamate (INCI: Isoamyl p-Methoxycinnamate), 3-(4-(2,2-bisethoxycarbonylvinyl)phenoxy)propenyl)methoxysiloxane/dimethylsiloxane copolymer, which is available, for example, under the trade name Parsol® SLX from Hoffmann La Roche.

Preferred further inorganic pigments are metal oxides and/or other metal compounds which are insoluble or sparingly soluble in water, in particular oxides of zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals, and mixtures of such oxides, and also the sulphate of barium ($BaSO_4$).

According to the invention, the pigments may advantageously be surface-treated ("coated"), the intention being to form or retain, for example, a hydrophilic, amphiphilic or hydrophobic character. This surface treatment can consist in providing the pigments with a thin hydrophilic and/or hydrophobic inorganic and/or organic coat by methods known per se.

Inorganic surface coatings for the purposes of the present invention may consist of aluminium oxide ($Al_2O_3$), aluminium hydroxide $Al(OH)_3$, or aluminium oxide hydrate (also: alumina, CAS No.: 1333-84-2), sodium hexametaphosphate ($NaPO_3)_6$, sodium metaphosphate ($NaPO_3)_n$, silicon dioxide ($SiO_2$) (also: silica, CAS No.: 7631-86-9), or iron oxide ($Fe_2O_3$). These inorganic surface coatings may be present on their own, in combination and/or in combination with organic coating materials.

Organic surface coatings for the purposes of the present invention may consist of vegetable or animal aluminium stearate, vegetable or animal stearic acid, lauric acid, dimethylpolysiloxane (also: Dimethicone), methylpolysiloxane (Methicone), simethicone (a mixture of dimethylpolysiloxane with an average chain length of from 200 to 350 dimethylsiloxane units and silica gel) or alginic acid. These organic surface coatings may be present on their own, in combination and/or in combination with inorganic coating materials.

Zinc oxide particles and predispersions of zinc oxide particles which are suitable according to the invention are obtainable under the following trade names from the companies listed:

| Trade name | Coating | Manufacturer |
| --- | --- | --- |
| Z-Cote HP1 | 2% Dimethicone | BASF |
| Z-Cote | / | BASF |
| ZnO NDM | 5% Dimethicone | H&R |
| MZ-303S | 3% Methicone | Tayca Corporation |
| MZ-505S | 5% Methicone | Tayca Corporation |

Further advantageous pigments are latex particles. Latex particles advantageous according to the invention are those described in the following specifications: U.S. Pat. No. 5,663,213 and EP 0 761 201. Particularly advantageous latex particles are those which are formed from water and styrene/acrylate copolymers and are available, for example, under the trade name "Alliance SunSphere" from Rohm & Haas.

Further advantageous UV-A filter substances for the purposes of the present invention are hydroxybenzophenones which are characterized by the following structural formula:

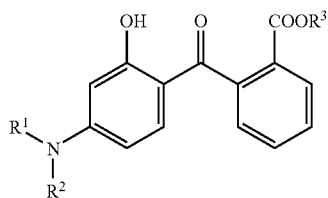

in which
R$^1$ and R$^2$, independently of one another, are hydrogen, C$_1$-C$_{20}$-alkyl, C$_3$-C$_{10}$-cycloalkyl or C$_3$-C$_{10}$-cycloalkenyl, where the substituents R$^1$ and R$^2$, together with the nitrogen atom to which they are bonded, can form a 5-membered or 6-membered ring and
R$^3$ is a C$_1$-C$_{20}$-alkyl radical.

A particularly advantageous hydroxybenzophenone for the purposes of the present invention is hexyl 2-(4'-diethylamino-2'-hydroxybenzoyl)benzoate (also: Aminobenzophenone), which is characterized by the following structure:

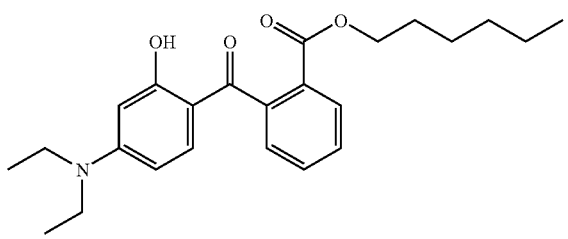

and is available under Uvinul A Plus from BASF.

Advantageous further UV-B filter substances for the purposes of the present invention are sulphonated, water-soluble UV filters, such as, for example:

Salts of 2-phenylbenzimidazole-5-sulphonic acid, such as its sodium, potassium or its triethanolammonium salt, and the sulphonic acid itself with the INCI name Phenylbenzimidazole Sulphonic Acid (CAS No. 27503-81-7), which is available, for example, under the trade name Eusolex 232 from Merck, or under Neo Heliopan Hydro from Haarmann & Reimer.

Advantageous UV filter substances for the purposes of the present invention are also so-called broadband filters, i.e. filter substances which absorb both UV-A and also UV-B radiation.

Advantageous broadband filters or UV-B filter substances are, for example, triazine derivatives, such as, for example, Dioctylbutylamidotriazone (INCI: Diethylhexylbutamidotriazone), which is available under the trade name UVASORB HEB from Sigma 3V;

Tris(2-ethylhexyl) 4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

An advantageous broadband filter for the purposes of the present invention is also 2,2'-methylenebis(6-(2H-benzotriazol-2-yl)-4-(1,1,3,3-tetramethylbutyl)phenol), which is available under the trade name Tinosorb® M from CIBA-Chemikalien GmbH.

For the purposes of the present invention, an advantageous broadband filter is also 2-(2H-benzotriazol-2-yl)-4-methyl-6-[2-methyl-3-[1,3,3,3-tetramethyl-1[(trimethylsilyl)oxy]disiloxanyl]propyl]phenol (CAS No.: 155633-54-8) with the INCI name Drometrizole Trisiloxane.

The further UV filter substances may be oil-soluble. Advantageous oil-soluble filter substances are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethyl-amino)benzoate, amyl 4-(dimethylamino) benzoate;

esters of benzalmalonic acid, preferably di(2-ethylhexyl) 4-methoxybenzal-malonate;

esters of cinnamic acid, preferably 2-ethylhexyl 4-methoxycinnamate, isopentyl 4-methoxycinnamate.

derivatives of benzophenone, preferably 2-hydroxy-4-methoxybenzophenone, 2-hydroxy-4-methoxy-4'-methylbenzophenone, 2,2'-dihydroxy-4-methoxy-benzophenone and UV filters bonded to polymers.

The list of given UV filters which can be used for the purposes of the present invention is not of course intended to be limiting.

The preparations according to the invention advantageously comprise the substances which absorb UV radiation in the UV-A and UV-B region in a total amount of, for example, from 2.0% by weight to 40% by weight, preferably from 3.0 to 35% by weight, in particular 5.0 to 30% by weight, in each case based on the total weight of the preparations, in order to provide cosmetic preparations which protect the hair and/or the skin from the entire range of ultraviolet radiation.

The examples below are intended to illustrate the present invention without limiting it. The numerical values in the examples are percentages by weight, based on the total weight of the particular preparations.

EXAMPLES

| | W/O emulsions | | | | |
|---|---|---|---|---|---|
| | 1 | 2 | 3 | 4 | 5 |
| PEG-30 dipolyhydroxystearate | 2.00 | 4.00 | 1.00 | 2.00 | 1.00 |
| Cetyldimethicone copolyol | 4.00 | | | 2.50 | 3.00 |
| Polyglyceryl-2 dipolyhydroxystearate | | | 3.00 | | 1.00 |
| Isostearyl diglyceryl succinate | | | 0.75 | | 0.30 |
| Lauryl methicone copolyol | | | | 2.00 | |
| Polysorbate-65 | | 2.00 | | | 1.50 |
| PEG-100 stearate | | | | 1.20 | 0.70 |
| Cetearyl sulphate | | | 0.25 | | 1.00 |
| Dimethicone | | 4.00 | 5.00 | | 2.00 |
| Cyclomethicone | 10.00 | 5.00 | | 5.00 | 3.00 |
| UVASorb ® K2A | | | | 0.50 | |
| Uvinul ® A Plus | | 2.00 | | 4.00 | |
| Bisethylhexyloxyphenol methoxyphenyltriazine | 1.00 | | | 0.50 | |
| Drometrizole trisiloxane | | | | 1.00 | |
| Phenylbenzimidazolesulphonic acid | | | 0.50 | | |
| 4-Methylbenzylidenecamphor | 4.00 | | | | |
| Methylenebisbenzotriazolyltetramethylbutylphenol | | | | | 3.00 |
| Ethylhexyl methoxycinnamate | 3.00 | 5.00 | | | 10.00 |
| Diethylhexylbutamidotriazone | | 1.00 | | | 6.50 |
| Ethylhexyltriazone | 3.00 | | | | 4.00 |
| Ethylhexyl salicylate | | | 5.00 | | 3.50 |
| Octocrylene | 3.00 | 5.00 | 1.00 | 2.00 | 2.00 |
| Butylmethoxydibenzoylmethane | 3.00 | 2.00 | 1.50 | 3.00 | 4.00 |
| Titanium dioxide T805 | 5.00 | 4.00 | 2.00 | 6.00 | 6.00 |
| Zinc oxide Z-Cote | 2.00 | | | | 1.00 |
| Dicaprylyl carbonate | 5.00 | | 15.00 | | 4.00 |
| Isopropyl stearate | | | 5.00 | 5.00 | |
| Butylene glycol dicaprylate/dicaprate | | 5.00 | | | 3.00 |
| Dihexyl carbonate | | 5.00 | | | |
| C12-15 alkyl benzoate | 7.00 | | 10.00 | | |
| Mineral oil | 5.00 | | | | 6.00 |
| Coconut fatty acid glyceride | | 2.00 | | 5.00 | |
| PVP hexadecene copolymer | | 0.75 | | | 0.40 |
| Glycerol | 5.00 | 12.50 | | 5.00 | 15.50 |
| Sorbitol | 5.00 | | 10.00 | | |
| α-Glucosylrutin | | | | | 0.15 |
| EDTA | | 0.15 | 0.03 | | 0.15 |
| Glycine soya | 0.75 | | | 1.50 | |
| Magnesium sulphate | 0.75 | 1.00 | | 0.45 | 1.00 |
| DMDM hydantoin | | 0.05 | | | 0.10 |
| Phenoxyethanol | 1.00 | 0.75 | 0.50 | | 1.00 |
| Alcohol | 2.00 | | | 5.00 | 1.00 |
| NaOH 45% | | | 0.40 | | |
| Dye, oil-soluble | 0.02 | | | | |
| Perfume | 0.30 | 0.45 | 0.35 | | 0.15 |
| Water | ad 100 | ad 100 | ad 100 | ad 100 | ad 100 |

| | 6 | 7 | 8 | 9 | 10 | 11 |
|---|---|---|---|---|---|---|
| Cetyldimethicone copolyol | | | | | 1.00 | |
| PEG-30 dipolyhydroxystearate | 4.00 | 5.00 | 3.00 | 5.00 | 3.00 | 3.50 |
| Bisethylhexyloxyphenol methoxyphenyltriazine | | | 3.00 | 1.50 | | |
| Butylmethoxydibenzoylmethane | 2.00 | 3.00 | 4.00 | 1.50 | 1.50 | 4.00 |
| UVASorb ® K2A | | | | 2.00 | | |
| Uvinul ® A Plus | | 1.00 | | 3.00 | | |
| Phenylbenzimidazolesulphonic acid | | | | | 2.00 | |
| Ethylhexyl methoxycinnamate | | 8.00 | | | 5.00 | 4.00 |
| Diethylhexylbutamidotriazone | 3.00 | 1.00 | 2.00 | 1.00 | | 3.00 |
| Ethylhexyltriazone | | | | 2.00 | 4.00 | |
| Octocrylene | 2.00 | 2.00 | 3.00 | 3.00 | 2.00 | 2.50 |
| Drometrizole trisiloxane | 1.00 | | | | | |
| Titanium dioxide Uvinul ® T805 | 2.00 | 6.50 | 6.00 | 3.50 | 4.00 | |
| Titanium dioxide MT-100 TV | | | | | | 2.00 |
| Zinc oxide Z-Cote ® HP1 | | | | 3.00 | | |
| Mineral oil | 5.00 | | | 5.00 | | 8.00 |
| Coconut fatty acid glyceride | 4.00 | 6.50 | | 5.00 | | |
| C12-15 alkyl benzoate | | | 5.00 | 8.00 | 9.00 | |
| Dicaprylyl ether | 10.00 | 5.00 | 2.00 | | | 7.00 |

-continued

| W/O emulsions | | | | | | |
|---|---|---|---|---|---|---|
| Butylene glycol dicaprylate/dicaprate | 3.00 | | 9.00 | 7.00 | 8.00 | 4.00 |
| Cetyl dimethicone | 0.50 | 1.00 | 0.50 | | | |
| C18-36 fatty acid triglyceride | | 1.00 | 0.50 | 1.0 | | |
| Cyclomethicone | 2.00 | 3.00 | 3.00 | | | 2.00 |
| Na starch octenyl succinate | | 0.50 | 0.50 | 1.00 | | |
| PVP eicosene copolymer | 0.50 | | | | 1.50 | 1.00 |
| Trisodium EDTA | 1.00 | | 1.00 | 0.50 | 0.35 | |
| Ethylhexyloxyglycerol | | 0.30 | | | | 0.50 |
| Methylpropanediol | | | | | | 7.50 |
| Glycerol | 5.00 | 7.50 | 6.00 | 8.00 | 7.50 | 2.50 |
| Butylene glycol | | 2.50 | | | | |
| Glycine soya | | 1.00 | | | | |
| MgSO$_4$ | 1.00 | 0.50 | 0.30 | 0.30 | 0.50 | |
| Lactic acid & sodium salt of lactic acid | 1.00 | 0.50 | | | | 0.85 |
| Vitamin E | 0.50 | | 0.50 | 1.00 | | 1.00 |
| DMDM hydantoin | | 0.60 | | | 0.20 | |
| Methylparaben | 0.50 | | | | 0.15 | |
| Phenoxyethanol | 0.50 | 0.40 | 0.50 | 0.60 | 1.00 | 0.60 |
| Dihydroxyacetone | | | | | 5.50 | |
| Alcohol | 3.00 | | 2.00 | 3.00 | | 1.00 |
| Perfume | 0.20 | | 0.20 | 0.20 | | 0.20 |
| Water | ad 100 | ad 100 | ad 100 | ad 100 | ad 100 | ad 100 |

That which is claimed:

1. A light protective cosmetic or dermatological preparation, wherein the preparation comprises:
   (a) PEG-30 dipolyhydroxystearate,
   (b) 2-ethylhexyl 2-cyano-3,3-diphenylacrylate,
   (c) at least one dibenzoylmethane derivative, and
   (d) at least 2% by weight of titanium dioxide particles, based on a total weight of the preparation, the preparation being free of water-soluble UV-A filter substances.

2. The preparation of claim 1, wherein an amount of wax in the preparation is less than 1.5% by weight, based on the total weight of the preparation.

3. The preparation of claim 1, wherein an amount of wax in the preparation is less than 1% by weight, based on the total weight of the preparation.

4. The preparation of claim 1, wherein the preparation is free of additional emulsifiers.

5. The preparation of claim 1, wherein an amount of titanium dioxide in the preparation is greater than an amount of 2-ethylhexyl 2-cyano-3,3-diphenylacrylate and greater than an amount of the at least one dibenzoylmethane derivative.

6. The preparation of claim 1, wherein the preparation further comprises an oil phase fraction, which oil phase fraction is present in said preparation in an amount that is at least 35% by weight, based on the total weight of the preparation.

7. The preparation of claim 1, wherein the preparation further comprises a water phase fraction.

8. A composition in the form of an oil-in-water emulsion, wherein the composition comprises:
   an oil phase;
   an aqueous phase;
   PEG-30 dipolyhydroxystearate, and
   a UV-A filter which consists essentially of titanium dioxide particles, 2-ethylhexyl 2-cyano-3,3-diphenylacrylate and at least one dibenzoylmethane derivative.

9. The composition of claim 8, wherein an amount of the UV-A filter in the composition is at least 10% by weight, based on a total weight of the composition.

10. The composition of claim 8, wherein the composition further comprises one or more active ingredients selected from α-lipoic acid, phytoene, D-biotin, coenzyme Q10, α-glucosylrutin, carnitine, carnosine, isoflavonoids, creatine, taurine, β-alanine and 8-hexadecene-1,16-dicarboxylic acid.

11. The composition of claim 8, wherein the composition further comprises at least one of vitamin E and vitamin A in an amount of from about 0.001 to 10% by weight, based on a total weight of the composition.

12. The composition of claim 8, wherein an amount of PEG-30 dipolyhydroxystearate is from 1 to 5% weight percent, based on a total weight of the composition.

13. The composition of claim 8, wherein the at least one dibenzoylmethane derivative comprises at least one of 4-(tert-butyl)-4'-methoxydibenzoylmethane and 2,2'-methylenebis(6-(2H-benzotriazol-2-yl)-4-(1,1,3,3-tetramethylbutyl)phenol).

14. The composition of claim 8, wherein the composition further comprises one or more substances selected from preservatives, preservative aids, complexing agents, bactericides, perfumes, foaming substances, defoaming substances, dyes, pigments, thickeners, moisturizing substances, humectant substances, fillers, fats, oils, waxes, alcohols, polyols, polymers, foam stabilizers, electrolytes, organic solvents and silicone derivatives.

15. The composition of claim 8, wherein the composition has a viscosity of less than 10,000 mPa s.

16. A cosmetic or dermatogical composition, wherein the composition comprises from 2 to 5% by weight of PEG-30 dipolyhydroxystearate, based on a total weight of the composition; and a UV-A filter which consists essentially of 2-ethylhexyl 2-cyano-3,3-diphenylacrylate, at least one dibenzoylmethane derivative and at least 2% by weight of titanium dioxide particles, based on the total weight of the composition, said titanium dioxide particles having a coating thereon.

17. The composition of claim 16, wherein the coating is selected from aluminium hydroxide/stearic acid, alumina/simethicone, octyltrimethylsilane, and alumina/silica.

18. The composition of claim 16, wherein an amount of titanium dioxide particles is from about 2 to 6.5% by weight, based on the total weight of the composition.

19. The composition of claim 16, wherein the composition further comprises a UV-B filter.

20. The composition of claim 16, wherein the composition further comprises a water phase and an oil phase.

* * * * *